(12) United States Patent  
Rachlin

(10) Patent No.: US 7,198,901 B1  
(45) Date of Patent: Apr. 3, 2007

(54) REFLECTIVE SUBSTRATE AND ALGORITHMS FOR 3D BIOCHIP

(75) Inventor: Daniel J. Rachlin, San Jose, CA (US)

(73) Assignee: Biocept, Inc., San Diego, CA (US)

( * ) Notice: Subject to any disclaimer, the term of this patent is extended or adjusted under 35 U.S.C. 154(b) by 441 days.

(21) Appl. No.: 10/664,248

(22) Filed: Sep. 16, 2003

Related U.S. Application Data

(60) Provisional application No. 60/412,522, filed on Sep. 19, 2002.

(51) Int. Cl.
*C12Q 1/68* (2006.01)
*C12M 1/36* (2006.01)
*G01N 15/06* (2006.01)

(52) U.S. Cl. .................. 435/6; 435/283.1; 435/287.2; 435/287.8; 435/288.7; 422/68.1; 422/82.05

(58) Field of Classification Search ..................... None
See application file for complete search history.

(56) References Cited

U.S. PATENT DOCUMENTS 5,418,136 A * 5/1995 Miller et al. ................ 435/5
5,776,785 A * 7/1998 Lin et al. .................... 436/527
6,320,991 B1 * 11/2001 Challener et al. ........... 385/12

2003/0013130 A1  1/2003  Charych et al. ............. 435/7.1
2003/0017508 A1  1/2003  Charych et al. ............. 435/7.9

OTHER PUBLICATIONS

D. Rachlin, "Optimized Approach for Microassay Screening," Proc. SPIE, (Jun. 2002), vol. 4623, p. 13-26.

* cited by examiner

*Primary Examiner*—B J Forman
(74) *Attorney, Agent, or Firm*—Fitch, Even, Tabin & Flannery

(57) ABSTRACT

A reflective substrate is used to amplify the photon signal captured from overlying analyte domains containing photon emitters. The reflective substrate provides substantial desired signal amplification of the photon emissions from each domain via interference effects induced in the incident excitation and/or emission energies. A dielectric is interposed between the domains and the reflective surface, which has a thickness such that substantial destructive interference occurs with respect to emission photons or excitation photons or both at the attachment surface. When analyte domains have a three-dimensional structure such that a significant fraction of their volume extends at least ¼ wavelength above the attachment surface provided by the dielectric, substantial constructive signal amplification can take place of signals generated within the analyte domains. Destructive interference relating to emissions arising from the plane of attachment surface yields significant reduction in spurious background emissions.

16 Claims, 2 Drawing Sheets

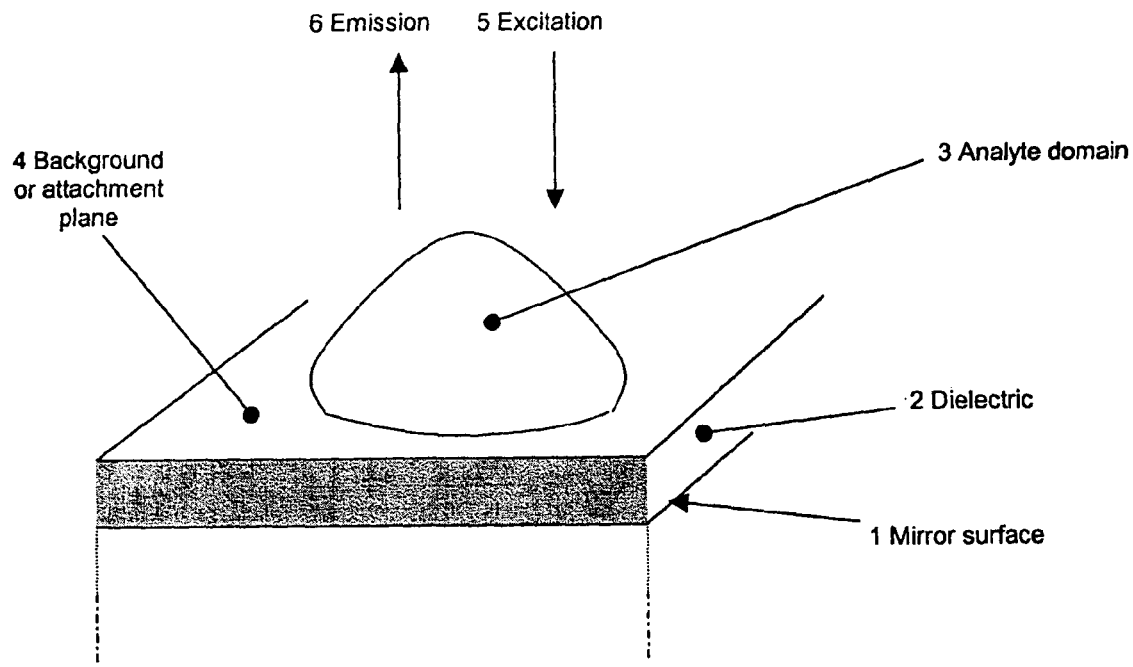
Figure 1 General concepts
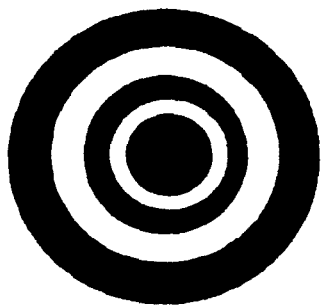
Figure 2. Common fluorescence pattern of domed analyte domain as viewed from above.

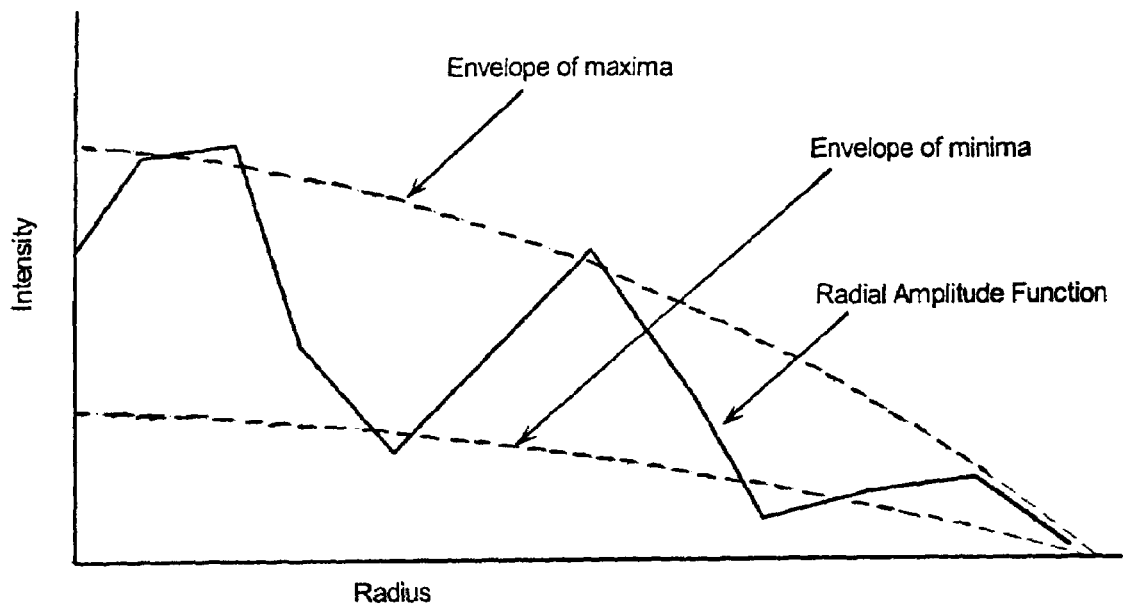
Figure 3. Radial function and envelope estimates.

REFLECTIVE SUBSTRATE AND ALGORITHMS FOR 3D BIOCHIP

This application claims priority from U.S. Provisional Application Ser. No. 60/412,522, filed Sep. 19, 2002, the disclosure of which is incorporated herein by reference.

BACKGROUND OF THE INVENTION

Biochip is a term used to refer to an array of discrete domains containing biochemical probes that will react with desired targets or analytes. Some means is generally necessary to quantify the amount of bound target, and it is common to employ some form of photon detection. Fluorescence or chemo-luminescence can be employed with spatially resolved fluorescence scanning being by far the most common detection approach. Such a fluorescence imaging system is described in detail in U.S. Pat. No. 5,672,880 (Sep. 30, 1997).

Because of the very small quantities of analyte normally encountered, highly sensitive means are required to detect photon emissions. A large industry has developed around producing scanners used in the detection of signals from biochips.

The present invention is based on the concept that constructive interference of an emission or excitation signal can occur with thin (e.g. ¼-wavelength) dielectrics on top of a reflective surface, such as aluminum or other metal. Constructive interference permits enhanced amplification of the signal over and above what may be achieved without a reflector, or beyond that which may hold for an incoherent radiation model. To create constructive interference, the fluorophore must lie at a particular distance from the surface of the mirror.

Kain, et al. in U.S. Pat. Nos. 6,008,892 and 6,177,990 disclose an approach to enhancing the detection of fluorescence from targets that are flat with respect to a wavelength. Their approach uses reflective substrates with a dielectric coating that is an odd multiple of a ¼ wavelength. More specifically, they teach the concept of creating constructive interference of the excitation, by employing a dielectric thickness that is ¼+N/2 wavelengths, where N is an integer greater than or equal to 0. They note that their approach yields substantial amplification of emission signal, with resultant enhancement of signal to noise ratio (SNR). The majority of biochips in current use tend to yield analyte distribution that is relatively flat with respect to an emission wavelength, making their invention effective in these cases. The aluminum surface eliminates background autofluorescence of underlying substrate. The approach amplifies background fluorescence from contaminants that are coplanar with the analyte regions. This form of background, often caused by failure to remove traces of excess flurophore, is amplified by the same factor as the desired signal.

Because a major problem with biochips is the presence of spurious background signal, much of which arises from the plane containing the standard analyte domains, i.e. the plane of attachment, the use of such a ¾-wave dielectric may not be the entire solution as this background may become amplified with the same gain as the signal from the analyte.

Some biochips are made using 3-dimensional analyte domains rather than the planar domains addressed in prior art; such domains may easily have a height that is ½ or more wavelengths. When placed upon a ¼-wave dielectric atop a reflective layer, amplification exists, but it is more complex as different parts of the domain experience constructive or destructive interference, resulting in some cases in distinct ring patterns if the domain is circularly domed. On average though, substantial amplification may be anticipated. At the plane of attachment for the analyte domains, constructive interference will exist both for points in the domain near this attachment plane, as well as for spurious background arising from within this plane.

In U.S. Pat. No. 6,174,683, Hahn et al. discuss a novel method for developing biochips that result in domed spots comprising a reactive target biomolecule immobilized in a hydrogel matrix. Probes with attached fluorophores can enter the matrix and combine with the target, resulting in a 3-dimensional fluorophore source distribution. Experiments have shown that this source distribution can be several optical emission wavelengths thick. An example is published in the paper "Optimized Approach for Microassay Scanning," D. Rachlin, Proc. SPIE, Vol 4623, p. 13–26 (June 2002) in which a pattern or concentric rings is demonstrated in the image of a fluorescent hydrogel spot that lies atop a reflective aluminum substrate. The rings are created by the alternating constructive and destructive interference over the varying thickness of the spot. The paper analyzes a ¼-wave approach and multi-wavelength thick substrate approaches.

Very generally, for 3-dimensional analyte domains, insofar as the total yield of amplified signal is concerned, there may be no "right" phase thickness of dielectric to promote amplification, so one may use a thickness of any phase with respect to a wavelength of interest.

SUMMARY OF THE INVENTION

This invention involves the use of a reflective substrate or coating and a transparent dielectric layer in the creation of biochips. The use of such combination has been extensively explored as a means to amplify a signal generated by a fluorophore. However, the current embodiment of the approach eliminates major background artifact emissions within the biochip.

Pursuant to this teaching, one selects a thickness of a dielectric that yields substantial cancellation at the wavelength of interest generated at its surface. Given a 180 degree phase shift at the reflective (metallic) surface, the thickness may then be an integer multiple of ½ wavelength. For example, if the emission photons are centered at 600 nm (in vacuum), one calculates the corresponding wavelength (600/refractive index) in the dielectric medium of interest, and then uses a thickness that is some integer multiple of ½ the calculated wavelength. The effect will be to eliminate background that emanates from the top surface of the dielectric i.e. the attachment surface. Cancellation occurs for background emissions that lie within and at the base of the analyte domain, in addition to its neighborhood.

In one particular aspect, the invention provides a substrate for a biochip comprising a flat optical mirror surface, which mirror reflects incident excitation and/or emission photons, and a transparent dielectric layer coating said surface, said layer having properties such that, for a set or range of reference wavelengths, the dielectric possesses a thickness such that destructive interference occurs for at least one of the following conditions at the surface of the dielectric opposite the mirror: for incident excitation light energy, destructive interference occurs between radiation propagating toward the mirror through the dielectric and reflected excitation radiation propagating away from the mirror, and for light energy emitted via spontaneous emission, scattering or other process, destructive interference occurs between wavefronts emitted or scattered toward the direction away from the mirror and wavefronts emitted or scattered toward the mirror and reflected by the mirror.

In another particular aspect, the invention provides a substrate for a biochip comprising a flat optical mirror surface which reflects incident excitation and/or emission photons, a transparent dielectric layer coating said surface, and a plurality of three-dimensional domains attached to the surface of said dielectric layer which yield detectable photon energy corresponding to the presence of analyte within a domain as a result of spontaneous emission, scattering or other mechanism, said dielectric layer having properties such that, for a set or range of reference wavelengths, the dielectric thickness is such that net destructive interference occurs for at least one of the following conditions at the exposed surface of the dielectric opposite the mirror: for incident excitation light energy destructive interference occurs between radiation propagating toward the mirror through the dielectric and reflected excitation radiation propagating away from the mirror, and for light energy emitted via spontaneous emission, scattering or other process, destructive interference occurs between wavefronts emitted or scattered toward the direction away from the mirror and wavefronts emitted or scattered toward the mirror and reflected by the mirror.

In a further particular aspect, the invention provides a system for analyzing a sample for the presence of specific targets, which system comprises a biochip that includes a flat optical mirror surface which reflects incident excitation and/or emission photons, one or more transparent dielectric layers coating said mirror surface, and a plurality of three-dimensional domains attached to an exposed surface of said dielectric layer yielding detectable photon energy corresponding to the presence of analyte within the domain as a result of spontaneous emission, scattering or other mechanism, and an optical detection system that is adapted to quantify the presence of analyte by measuring or imaging photons associated with each analyte domain, said dielectric layer or layers having a thickness and refractive index such that for a set or range of reference wavelengths, net destructive interference occurs for at least one of the following conditions at the exposed surface of the dielectric: for incident excitation light energy destructive interference occurs between radiation propagating toward the mirror through the dielectric and reflected excitation radiation propagating away from the mirror, and for light energy emitted via spontaneous emission, scattering or other process, destructive interference occurs between wavefronts emitted or scattered toward the direction away from the mirror and wavefronts emitted or scattered toward the mirror and reflected by the mirror.

In a still further particular aspect, the invention provides a method of analysis using a system provided by the invention wherein a brightness pattern is first identified and such pattern is then used to estimate one or more of the following parameters:

a. morphological symmetry and regularity of the domain, including circular symmetry,
b. conformance of the brightness pattern to an expected set of patterns, and
c. physical dimensions of the domain based upon counting the number of bright or dark contours and using knowledge of the wavelengths within dielectric and analyte domain.

BRIEF DESCRIPTION OF FIGURES

FIG. 1 schematically depicts basic features of the invention.

FIG. 2 depicts an emission pattern that is associated with a domed 3-dimensional fluorescent analyte domain when imaged from above.

FIG. 3 depicts estimates of radial functions and envelopes.

DESCRIPTION OF PREFERRED EMBODIMENTS

Very generally, the invention provides a substrate for a biochip comprising a flat optical mirror surface which reflects incident excitation and/or emission photons and which is coated with a transparent dielectric layer. This layer is selected to have properties such that, for a set or range of reference wavelengths, its thickness is such that destructive interference occurs for at least one of the following conditions at its exposed surface:

i. for incident excitation light energy, destructive interference occurs between radiation propagating toward the mirror through the dielectric and reflected excitation radiation propagating away from the mirror, and
ii. for light energy emitted via spontaneous emission, scattering or other processes, destructive interference occurs between (a) wavefronts emitted or scattered in a direction away from the mirror and (b) wavefronts emitted or scattered toward the mirror and reflected by the mirror.

Generally, the thickness of the dielectric is chosen to be approximately N/2 wavelengths, where N is any integer greater than 0. Preferably, the mirror is a metallic film deposited upon a flat substrate, e.g. aluminum or silver. The dielectric may be silicon dioxide or silicon monoxide or another suitable material known in this act, and its exposed surface may be treated with a suitable amine to facilitate the attachment of chemical compounds. The biochip substrate of 1 where the mirror is made of reflective aluminum or silver.

FIG. 1 schematically demonstrates features of the invention. A metallic reflective surface 1 (which may be deposited as a film upon a substrate as known in this art) is preferably coated with a transparent dielectric 2 having a thickness corresponding to N/2 wavelengths, where N>0. In some instances, it may be feasible to employ a biochip where N=0, i.e. where the domains are deposited directly on the reflective surface or nearly so. The dielectric provides a protective barrier for the metallic surface and may be used to provide chemical compatibility, even when its thickness is a fraction of a wavelength, i.e. where N=1. Moreover, in the alternative embodiment mentioned above, a very thin layer, for example 1–5% of a wavelength, i.e. nearly 0 thickness in terms of optical wavelength, will still provide desirable chemical or physical properties.

On top of the dielectric are deposited analyte domains 3 that are attached to upper surface 4 of the dielectric which lies at a distance from the mirror 1 such that destructive interference occurs on excitation, emission or both for a set or range of reference wavelengths for photon sources lying within the attachment plane. Maximum destructive interference occurs when the round-trip optical phase change for a wavefronts traveling from the attachment plane to the mirror surface and back is 180 degrees. Because the mirror is expected to produce a phase inversion, the dielectric thickness is therefore chosen to be an integer multiple of ½ wavelength. Excitation photons 5 are suitably applied to the sample treated region of the biochip, yielding emission (or scattering) 6 that can be detected if the domain has sequestered a sample during an assay.

To achieve full destructive cancellation at the attachment surface, it is preferred that the reflective surface possess as close to 100% reflectivity as possible. Although a reflective surface may be a polished metal surface, it is preferably a metallic film, e.g. aluminum, silver, gold, rhodium, etc. deposited on an appropriate substrate, such as a glass slide, a hard plastic plate or the like. The dielectric and any additional layers are preferred to be transparent as possible. Examples of suitable transparent dielectrics include $SiO_2$ and SiO. Optionally the attachment surface of the dielectric may be chemically treated, as with an amine, to promote strong attachment of the domains.

As described in the following section, the analyte domain is formed in a manner such that a significant optical signal may be generated that avoids the destructive interference cited here. In fact, it may be possible to generate some amplification through constructive interference.

Destructive interference may be designed to occur for both excitation photons and emission photons at reference wavelengths at the attachment plane. While there is an exact relationship between each reference wavelength and an optimum dielectric thickness to create the destructive interference, in reality this relationship is continuous, so that in fact significant partial destructive cancellation may occur for wavelengths offset slightly from the optimum. With (¼+N/2) lambda multiples representing full constructive interference, and (½+N/2) representing full cancellation, it is easy to see that a substantial degree of cancellation will occur when dielectric thickness lies within the range of ⅜+N/2 to ⅝+N/2.

The invention provides a biochip format in which the plane of the attachment surface of the analyte domain or domains is located at such a distance from the reflective surface that it is designed to effect destructive interference at reference wavelengths of background signals. A major advantage lies in the attenuation or elimination of signals arising from sources within or at this plane. It is common for spurious contaminants to become attached to this plane, yielding photons that interfere with the detection of analyte. Heretofore, estimates of this background have been subtracted, but the shot noise effects, as well as uncertainty in estimating this background persisted. An optical means to directly eliminate or very substantially attenuate the background becomes a very desirable advantage of this invention.

For analyte confined to the attachment plane, as in common with most biochips, the signal generated in the detection of analyte may be coherently cancelled as well; however, where the analyte domains have a height so that portions of the sample experience markedly reduced destructive interference, actual constructive interference may occur. For example, if analyte is present at levels above the attachment surface corresponding to ¼+N/2 wavelengths, N>=0, constructive interference can then occur, and such constructive interference may occur with incident and reflected excitation energy, or with emitted (or scattered) energy.

When the analyte domain is domed, the image formed using emitted photons may display concentric rings as seen in FIG. 2. One may expect these rings to have very high contrast if analyte is concentrated on the surface of the dome, with contrast being reduced as analyte becomes more uniformly distributed through the material. Hence, the pattern formed in the image can become useful for the following:

1. Determining the symmetry and regularity of the domain.
2. Determining the degree to which analyte is concentrated near the surface of the domain.

Because of the a-priori knowledge of the concentric ring structure, an algorithm that determines a measure of the integrated or mean emission within the spot can emphasize information from the region of strong signal, and de-emphasize information from areas of weak signal. Suppose for example that one is faced with a simple additive noise model (0-mean, constant gaussian power). The ring pattern can be inferred from the geometry of the spot, then used to generate a matched filter or template such that high weightings are applied to the regions of relative high predicted high amplitude. Here, "predicted" means that which would be expected in the absence of any noise (e.g. an ensemble mean). Note that for different noise models, such as shot noise in signal+additive noise, one can calculate a different weighting function. The net effect will still be one that emphasizes areas of constructive interference and de-emphasizes areas of destructive interference.

The ring pattern provides more detailed morphological information concerning the biochip. For example, a disruption of the regular pattern not attributable to noise can serve as an indicator of whether the spot has been corrupted in some way, as by a foreign particle or trauma.

It is common for an optical detection approach to yield one or more images of the set of analyte domains, where each analyte domain appears as an area of brightness with respect to the background because of enhanced signal fluorescence present within the domain. Relative attenuation of the background as a result of its destructive cancellation, should increase the contrast and hence detection of each domain.

An image of the analyte domains can be analyzed in any number of ways. It is to be understood that the invention does not rely upon the particulars of any one analytical approach used in processing the data. It is very common to identify through conventional image processing the bounds of each analyte domain captured within an image. The spatial arrangement of such domains as well as the morphological properties might be known to some extent beforehand, aiding in their identification within the image. For example, the domains might be arranged in a fixed Cartesian grid pattern, with specific known spacing amongst the rows and columns. In addition, the shapes or outline of the domains might be circular, with perhaps a diameter that falls within close tolerances. In other cases, the shape might be known, but the diameter inferred primarily through image analysis. In any case, it is understood that partial or complete a priori knowledge of the properties of the layout of the domains and their individual morphology should be of assistance in the image analysis procedure.

In the case of biochips, software-based image processing approaches very commonly implement rules to identify and analyze the image corresponding to the analyte domains. A large body of literature exists on this subject, in addition to many commercial implementations of software analysis techniques. After identifying the boundary of each domed domain—or spot—the signal might be estimated by subtracting an estimate of the background signal formed by looking at parts of the image outside the spots, and then summing up the background subtracted intensity values within each spot. This approach is quite common, and it has a number of variants, such as using median rather than average or summed signal levels within each spot. Other variants may involve summing the values after discarding outliers in the highest and/or lowest bins of an intensity histogram calculated for each spot. It is common to employ various "preprocessing" steps to assist in the software analysis, and such steps might include the use of median or convolution filters.

As noted above, analyte domains having a domed or other three-dimensional structure may result in a pattern of alternating bright and dark rings as demonstrated in FIG. 2. The contrast of these rings depends on a number of factors, such as the excitation and emission bandwidth, as well as the degree to which signal is concentrated on the surface of the three-dimensional domain as opposed to distributed evenly throughout. The number of rings is also dependent on certain factors, such as the height of the analyte domain with respect to its base.

The number, contrast and symmetry of the rings can be estimated using image analysis software. A basic algorithm is outlined as follows, and it is to be understood that there exists an infinite set of variants and refinements. As a first step, the image of each spot is identified possibly using a priori information as discussed above. The center is identified as perhaps the centroid of the intensity pattern after the background estimate is subtracted. One can then use a least-squared error approach to fit an arbitrary function that is radially symmetric about the centroid. Such as function will be defined by a set of weights corresponding to each radius of the brightness function being used in its argument. For example, the spot might typically be 10 pixels in diameter, so that one might use a set of radii ranging from 0 to 10 in steps of 1. In this case, there will be 11 unknown radial function values, and straightforward estimation approaches can be used to determine the set values such that the sum of squared errors between the actual values and the function estimates is a minimum. Since the actual intensity function is defined over a grid of pixels, interpolation or nearest neighbor assignments might be used to create an expression for the estimate at radii that are not within the discrete set. The degree of fit between the estimate and the measured intensity values can be calculated and then used to form an assessment of data quality and integrity.

Once the radial best-fit function is estimated, the properties and number of rings can be estimated by considering this function. For example, the function might have areas of local minima or maxima, corresponding to dark and bright rings respectively. The contrast between alternating light and dark rings can be defined in a number of simple ways, such as by taking the ratio of a local maximum with respect to the average of the two adjacent minima. An average contrast might then be calculated. The distance between the rings, as well as their phasing with respect to the center, can be identified, with phasing referring to questions of whether maximum (or minimum) occurs close to the center. The phasing pattern will depend on the height of the spot. There might be variability of the pattern due to the particulars of the excitation and emission spectra being used in the detection process. This phasing pattern variability might contribute to some variability among different measurements among spots that should yield otherwise similar amplitudes. Such a possibility might be addressed by using more advanced estimation approaches. For example, FIG. 3. shows a plot of (1) a radial amplitude (or intensity) function, along with an estimate of (2) a function that connects the maxima and a function (3) that connects the minima. It may be desirable to form a combined estimate using the two envelope functions by taking for example their average, and then using this new function to estimate the total spot signal, by for example summing up the individual function values. There are many approaches that may be made to this general form of analysis as well known in this art, and it is felt that use of such envelope or other similar functions should bring greater consistency to the estimation approach.

EXAMPLE

To test the arrangement, microspots were applied to substrates which contained a mixture of a polyurethane-based hydrogel and Cy5 fluorescent dye so as to form a series of three-dimensional tiny mounds or domains spaced apart on surfaces of the slides. Two different sets were used, the slides of one set were purchased from Corning and were transparent aminosilane-coated slides. The other set of slides were mirrored, having a thin aluminum film that was highly reflective, atop a thin substrate, with the aluminum being coated with a layer of silica of appropriate thickness. These microspots were deposited using two different pin sizes, one set of spots on each set of slides was deposited using large pins having a diameter of about 625 microns and a second set was deposited using small pins having a diameter of 350 microns. Once the microspots had polymerized, both sets of slides were imaged using a Perkin-Elmer ScanArray-Light microarray laser scanner that was set with the appropriate Cy5 laser and filter settings. Because all of the spots were of exactly the same material, the spots of each set would have the same size and fluorophore content. Testing showed that mirrored slide gave a 4 to 4.5 fold greater signal than the transparent Corning slides, as was expected. Background noise, however, only showed a three-fold increase for the mirrored slides, which is indicative of effective partial background cancellation at the surface of the slides.

Although the invention has been disclosed with regard to certain preferred embodiments which constitute the best mode presently known for carrying out the invention, it should be understood that various changes and modifications as would be obvious to one having the ordinary skill in the art may be made without departing from the scope of the invention which is set forth in the claims appended hereto. The disclosures of all U.S. patents and publications listed herein are expressly incorporated herein by reference.

Particular features of the invention are emphasized in the claims which follow:

The invention claimed is:

1. A system for analyzing a sample for the presence of specific targets in a biochip while eliminating major background emissions, which system comprises:
   a biochip that includes
   a flat optical mirror surface which reflects incident excitation and/or emission photons,
   one or more transparent dielectric layers coating said mirror surface, and
   a plurality of three-dimensional domains attached to an exposed surface of said dielectric layer yielding detectable photon energy corresponding to the presence of analyte distributed throughout the domain as a result of spontaneous emission, scattering or other mechanism, each domain being of a thickness equal to or greater than about one-half of an optical emission wavelength of said photon energy, and
   an optical detection system that is adapted to quantify the presence of analyte in each domain by measuring or imaging photons associated with each analyte domain, said dielectric layer or layers having a thickness which is approximately N/2 wavelengths, where N is any integer greater than 0 and a refractive index such that, for a set or range of reference wavelengths, net destructive interference occurs for at least one of the following conditions at the exposed surface of the dielectric:
  i. for incident excitation light energy, destructive interference occurs between radiation propagating toward the mirror through the dielectric and reflected excitation radiation propagating away from the mirror, and
  ii. for light energy emitted via spontaneous emission, scattering or other process occurring at about the exposed dielectric layer surface, destructive interference occurs between wavefronts emitted or scattered toward the direction away from the mirror and wavefronts emitted or scattered toward the mirror and reflected by the mirror,
whereby, for any sources of potential background photon contamination at the plane of said exposed surface, net destructive interference occurs at the set or range of reference wavelengths thereby diminishing any such contaminant optical signal.

2. The system of claim 1 wherein said optical detection system includes a source of excitation or illumination which is capable of inducing optical emission from such analyte.

3. The system of claim 1 wherein said detection system includes a laser scanner for imaging an identifiable pattern of source brightness distribution which can be used to estimate:
  i. the three-dimensional morphology of the domains containing analyte, and
  ii. the distribution of analyte within the three-dimensional structure of the domain.

4. The system of claim 3 wherein said laser scanner includes means for integrating the brightness over the entire image of the domain to approximate the quantity of domain analyte.

5. The system of claim 3 wherein said laser scanner includes means for estimating analyte quantity from the brightness pattern by integrating the brightness over the entire image of the domain, with greater weighting given to those regions with greater mean brightness.

6. The system of claim 1 where said mirror surface is a metallic film deposited upon a flat substrate.

7. The system of claim 6 where the mirror surface is made of reflective aluminum or silver.

8. The system of claim 1 where the dielectric layer is silicon dioxide or silicon monoxide.

9. The system of claim 1 where the exposed dielectric layer surface is modified to have free amine groups.

10. A method of analysis using the system of claim 1 wherein a brightness pattern is first identified and such pattern is then used to estimate one or more of the following parameters:
  i. morphological symmetry and regularity of the domain, including circular symmetry,
  ii. conformance of the brightness pattern to an expected set of patterns, and
  iii. physical dimensions of the domain based upon counting the number of bright or dark contours and using knowledge of the wavelengths within the dielectric and analyte domain.

11. The method of claim 10 wherein such conformance is measured relative to a scenario where analyte is uniformly distributed within the domain.

12. The method of claim 10 wherein such conformance is measured relative to a scenario where analyte is concentrated on the surface of the domain.

13. A system for analyzing a sample for the presence of specific targets in a biochip while eliminating major background emissions, which system comprises:
  a biochip that includes
    a flat optical mirror surface which reflects incident excitation and/or emission photons,
    one or more transparent dielectric layers coating said mirror surface, and
    a plurality of three-dimensional domains attached to a top flat surface of said dielectric layer, each domain yielding detectable photon energy corresponding to the presence of analyte distributed throughout the domain as a result of spontaneous emission, scattering or other mechanism, each domain being of a thickness equal to or greater than about one-half of an optical emission wavelength of said photon energy, and
  an optical detection system that is adapted to quantify the presence of analyte in each domain by measuring or imaging photons associated with each analyte domain,
    said dielectric layer or layers having a thickness which is approximately N/2 wavelengths, where N is any integer greater than 0 and a refractive index such that, for light energy having a range of reference wavelengths emitted via spontaneous emission, scattering or other process occurring at about the top surface of said dielectric layer, destructive interference occurs between wavefronts emitted or scattered toward the direction away from the mirror and wavefronts emitted or scattered toward the mirror surface and reflected by the mirror surface,
    whereby such net destructive interference which occurs at the range of reference wavelengths diminishes any contaminant optical signal from sources of potential background photon contamination at said top flat surface.

14. The system of claim 13 wherein said optical detection system includes a source of excitation or illumination which is located above said top surface and which is capable of inducing optical emission from such analyte.

15. The system of claim 13 wherein said detection system includes a laser scanner for imaging an identifiable pattern of source brightness distribution which can be used to estimate:
  i. the three-dimensional morphology of the domains containing analyte, and
  ii. the distribution of analyte within the three-dimensional structure of the domain.

16. The system of claim 13 wherein said laser scanner includes means for integrating the brightness over the entire image of the domain to approximate the quantity of domain analyte.

* * * * *